United States Patent [19]

Huber et al.

[11] Patent Number: 5,595,741
[45] Date of Patent: Jan. 21, 1997

[54] AMINOALKYLMALEIMIDES AND HAPTEN AND ANTIGEN DERIVATIVES DERIVED THEREFROM AS WELL AS CONJUGATES WITH PEPTIDES OR PROTEINS

[75] Inventors: Emasmus Huber, Unterfinning; Christian Klein, Weilheim; Hans-Georg Batz, Tutzing; Bruno Zink, Uffing, all of Germany

[73] Assignee: Boehringer Mannheim GmbH, Mannheim, Germany

[21] Appl. No.: 278,621

[22] Filed: Jul. 21, 1994

Related U.S. Application Data

[62] Division of Ser. No. 656,051, filed as PCT/EP90/00957, Jun. 16, 1990, abandoned.

[30] Foreign Application Priority Data

Jun. 19, 1989 [DE] Germany .................... 39 19 915.0

[51] Int. Cl.[6] .................... C08L 77/04; A61K 37/02; A61K 39/385
[52] U.S. Cl. .................... 424/194.1; 530/405; 530/403; 548/546
[58] Field of Search .................... 548/546; 424/194.1; 530/405, 403

[56] References Cited

U.S. PATENT DOCUMENTS

| | | | |
|---|---|---|---|
| 4,276,206 | 6/1981 | Katz | ........................ 424/194.1 X |
| 4,902,506 | 2/1990 | Anderson et al. | ........................ 424/194.1 O |

Primary Examiner—David B. Springer
Attorney, Agent, or Firm—Felfe & Lynch

[57] ABSTRACT

The invention concerns new aminoalkylmaleimides of the general formula I

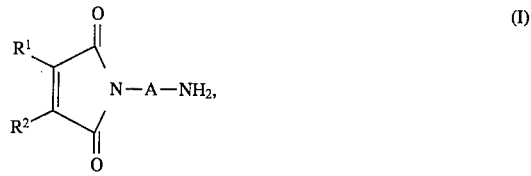

in which $R_1$ and $R_2$ are the same or different and represent hydrogen or a $C_1$–$C_4$ alkyl group and A represents a straight-chain or branched, saturated or unsaturated alkylene group with 2 to 6 carbon atoms which is interrupted, if desired, by an oxygen or sulphur atom or a carbonyl group, as well as their corresponding acid addition salts.

The present invention also concerns amidoalkylmaleimide derivatives formed from compounds of the general formula I and immunological binding partners. In addition, the invention concerns immunological conjugates which can be produced by reaction of the amidoalkylmaleimide derivatives with peptides or proteins.

The subject matter of the present invention are also the corresponding processes of production of the compounds according to the present invention as well as the use of these conjugates in diagnostic methods of determination, in particular in immunoassays.

10 Claims, No Drawings

AMINOALKYLMALEIMIDES AND HAPTEN AND ANTIGEN DERIVATIVES DERIVED THEREFROM AS WELL AS CONJUGATES WITH PEPTIDES OR PROTEINS

This is a Divisional Application of application Ser. No. 07/656,051, filed Feb. 14, 1991, now abandoned.

The invention concerns new aminoalkylmaleimides of the general formula I

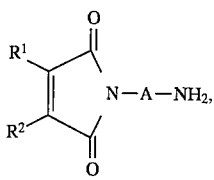

in which $R_1$ and $R_2$ are the same or different and denote hydrogen or a $C_1$–$C_4$-alkyl group and A represents a straight-chain or branched, saturated or unsaturated alkylene chain with 2 to 6 carbon atoms which is interrupted, if desired, by an oxygen or sulphur atom or a carbonyl group, as well as their corresponding acid addition salts, except the compound N-6-aminohexylmaleimide.

The present invention also concerns the amidoalkylmaleimide derivatives of the general formula II formed from compounds of the general formula I and immunological binding partners

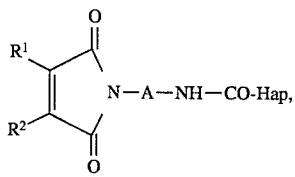

in which $R_1$, $R_2$ and A have the meaning mentioned above and Hap, which is a residue formed by amidation from an immunological binding partner carrying one or several carboxyl groups or activated carboxyl groups. Haptens or antigens come, for example, into consideration as immunological binding partners.

In addition, the invention concerns immunological conjugates which can be produced by reaction of compounds of the general formula II with peptides or proteins. These conjugates are described in the following by the term hapten-peptide or antigen-peptide conjugate.

The subject matter of the present invention are also processes for the production of compounds of the general formulae I and II as well as peptide and protein conjugates and the use of these conjugates in diagnostic methods of determination, in particular in immunoassays.

The linking of two components or compounds which differ functionally is of fundamental importance in many biochemical techniques. Thus, for example, in the field of affinity chromatography different ligands are bound to a solid insoluble carrier matrix. These ligands are able to recognise and bind substances which are contained in the sample and which are specific for this particular ligand. A specific isolation of the compounds contained in the sample is possible by this means. Antibodies or enzymes which specifically bind an antigen or substrate come, for example, into consideration as ligands.

Bifunctional reagents which are also denoted linkers are often used to link components in the above sense. These contain, as a rule, two chemically reactive groups which react as specifically as possible with particular residues of the components which are to be linked together. In this connection one in general differentiates between heterobifunctional reagents on the one hand such as e.g. gamma-maleimido-butyric acid-N-hydroxysuccinimide or m-maleimido-benzoyl-N-hydroxysuccinimide ester (MBS), and homobifunctional reagents on the other hand such as e.g. N,N'-bis-(3-maleimidopropionyl)-2-hydroxy-1,3-propanediamine. The heterobifunctional reagents have two chemically different reactive groups such as, for example, the maleimido and the N-hydroxysuccinimido group in the case above. While the maleimido group reacts very specifically with compounds containing sulfhydryl, the hydroxysuccinimido group is preferably suited for reaction with compounds which contain an amino group. By this means two components or compounds may be linked together in an elegant manner, in which, for example, one of them contains a sulfhydryl group and the other contains an amino group. In an analogous manner, homobifunctional reagents, which contain two chemically reactive groups of the same kind, serve to link components with identical functional groups as for example in the above case of sulfhydryl groups.

Depending on the property of the components which are to be linked together, a series of such bifunctional reagents may be used accordingly (Kia-ki Han et al., Int. J. Biochem. 16 (2), 129–145 (1984) and R. E. Feeney, Int. J. Peptide Protein Res. 29, 1987, 145–161). Thus, for example, the use of N-6-aminohexylmaleimide for the production of a modified agarose solid phase for affinity chromatography is described in Arch. Biochem. Biophys. 203, 774 (1980).

Furthermore, the production of immunogens is known from the state of the art, as, for example the European Patent Application EP-A-0,142,193 in which suitable antigens such as polypeptides, oligosaccharides or oligonucleotides are bound to reactive groups of hydrophobic compounds such as, for example, phospholipids, which are complexed by at least one group of glycosides, preferably saponins, with a hydrophilic and a hydrophobic part. In particular, a β-endorphin derivative is described in Example 4 of this European Patent Application in which an amino acid of this dodecapeptide is modified by a maleimido-butylamine group. However, the application does not contain any details on how such a derivative can be produced.

A further area of application for bifunctional reagents is the production of reagents for clinical diagnosis. For this purpose, methods of determination based on immunoassays which are distinguished by their very high sensitivity are being carried out in increasing numbers. In doing so, conjugates are often used which, for example, consist of an enzyme label and a substance to be determined, the so-called analyte, or a substance capable of binding an antibody the so-called antigen. These conjugates can be preferably produced by the use of bifunctional reagents.

A further recent example is the so-called CEDIA technique (Clinical Chemistry 32/9, 1637–1641 (1986); U.S. Pat. No. 4,708,929) which is becoming increasingly important in the field of homogeneous immunoassays. In this diagnostic method of determination use is also made of the principle of linking two compounds. In this process an analyte, which in general can be a hapten or an antigen, is linked to an enzymatically inactive precursor of the enzyme β-galactosidase. This inactive precursor is a peptide and is also denoted enzyme donor in the literature cited above. Since then, a series of different peptides are known to function as enzyme donors such as e.g. ED4.

The principle of this test procedure is as follows: The enzyme β-galactosidase consists of four subunits, which in turn are composed of a larger polypeptide chain, which is also designated as enzyme acceptor EA, and a smaller peptide chain called the enzyme donor ED. Enzyme acceptor and enzyme donor are both enzymatically inactive but can spontaneously aggregate to form an active tetramer. As a consequence of the extraordinarily small dissociation constant of the active enzyme formed from enzyme donor and enzyme acceptor, the amount of enzyme formed is directly proportional to the amount of enzmye donor or enzyme acceptor available. When carrying out immunoassays one makes use of this property by using a chemically modified enzyme donor instead of the natural enzyme donor. A special feature of this is that an analyte is covalently linked to functional groups of the enzyme donor. Haptens or antigens, for example, come into consideration as the analyte. The test system used for the immunological method of determination contains in addition an antibody which recognises a specific immunogen of the respective analyte. In this connection, the antibody does not usually differentiate between free analyte and analyte covalently bound to the enzyme donor. The antibody is present in an amount sufficient to completely bind the enzyme donor conjugates modified with the analyte which are present in the test system.

As a result, the enzyme donor and the enzyme acceptor are prevented from spontaneously associating to form the active enzyme.

The reaction to determine the concentration of an analyte is carried out in such a way that a defined amount of the sample to be determined is added to the test system described above. Since this type of reaction is a competitive test, the antibodies present which are directed against the analyte bind the free analyte derived from the sample as well as part of the enzyme donor labelled with the analyte. The free portion of the labelled enzyme donor released by the free analyte in a displacement reaction associates spontaneously with the enzyme acceptor to form the enzymatically active β-galactosidase tetramer, the concentration of which is directly proportional to the concentration of the analyte derived from the sample. The amount, or specific activity by volume, of the enzyme β-galactosidase formed by this spontaneous association is measured by hydrolysis of a suitable enzyme substrate, for example of o-nitrophenyl-β-D-galactopyranoside or chlorophenol red-β-D-galactopyranoside, and release of the corresponding chromophore.

A problem associated with the linkage which is necessary between immunogen (analyte) and enzyme donor as described above is that the modification of the enzyme donor may only be carried out at those positions in the molecule which are not of importance for the recognition between enzyme donor and enzyme acceptor. Otherwise the association to form the enzymatically active enzyme complex would be disturbed and the measured value for the hapten to be determined would simulate a false result.

It is known from the literature that, for example, maleimidyl-benzcarbamyl-digoxigenin (Clin. Chem. 32, 1637 (1986)) can be used as the hapten-enzyme donor conjugate. The binding of the hapten digoxigenin to the enzyme donor is carried out by reaction with 3-maleimido-benzoic acid-isocyanate. The linkage of the enzyme donor with the digoxigenin derivative formed above is carried out by reacting a sulfhydryl group of the amino acid cysteine on the enzyme donor with the maleimido group.

The bifunctional reagent used in the above-mentioned case has, however, the disadvantage that on the one hand the urethane bond which is present is sensitive to hydrolysis and thus the reagent is not sufficiently stable and that in addition, as a result of the presence of a benzcarbamyl residue, part of the binding activity of the antibody is directed against the linker itself i.e. against the bridging molecule between hapten and enzyme donor in the immunogen. This means that cross-reactivities would be expected to occur frequently which leads to inaccuracies in the immunological test during the determination.

Another problem is that the bifunctional reagents used should be as stable as possible and simple to produce. In addition, it is desirable that they react with haptens or antigens under conditions which are as mild as possible and as a consequence the hapten-peptide derivatives capable of being used as immunogens for the immunization and isolation of antibodies can be produced in a mild and simple manner.

A disadvantage of heterobifunctional reagents with a maleimido group is, however, that they are often very reactive and hydrolyse easily to maleic acid derivatives. As a result of their high reactivity they are often less specific for sulfhydryl groups, in particular if they are used in stoichiometric amounts. This low specificity can lead to complex reaction mixtures which form when the maleimido group reacts with other reactive groups of the peptides or proteins to be linked, such as e.g. with amines. Such side reactions lead to undesired reaction mixtures which are often difficult to separate. The conjugates produced must, however, be of the highest purity in order to obtain antibodies by immunization which have as high a specificity as possible and low cross-reactivity.

It was therefore the object to provide new bifunctional reagents which do not exhibit the disadvantages mentioned above.

It was found that, surprisingly, the compounds according to the present invention of formula I can be used advantageously as heterobifunctional reagents. In particular it has turned out that the group A located between the maleimido and the amino group is responsible for a low cross-reactivity of the antibodies produced with the aid of the hapten-peptide conjugate. This applies especially for the short chain derivatives with a chain length in A of 2–5, in particular of 2, 3 or 4 atoms.

$R_1$ and $R_2$ in the formula I can be the same or different and each denote a hydrogen atom or a $C_1$–$C_4$-alkyl group such as e.g. the methyl, ethyl or isopropyl group. However, $R_1$ and $R_2$ preferably represent a hydrogen atom. The group A denotes a straight-chain or branched, saturated or unsaturated alkylene group with 2–6, preferably 2–4 C atoms which is interrupted, if desired, by an oxygen or a sulphur atom or by a carbonyl group. In this sense the following meanings come into consideration: $A=-(CH_2)_n-$; $-(CH_2)_m-CH(CH_3)-(CH_2)_o-$; $-(CH_2)_m-C(CH_3)_2-(CH_2)_o-$; $-(CH_2)_m-X-(CH_2)_o-$ whereby $X=O,S,CO$; $-(CH_2)_m-CH=CH-$ whereby n=2–6 and m=o=1–4 and m+o=2–5. A preferably denotes the groups $-(CH_2)_n-$ whereby n=2,3,4 or 5 and $-CH_2-O-CH_2-$, $-CH_2-S-CH_2-$, $-CH_2-CO-CH_2-$.

Acid addition salts of amines are salts with organic or inorganic acids such as e.g. acetic acid or hydrochloric acid.

Compounds of formula I can, for example, be produced in such a way that a diamine having the general formula III

$$H_2N-A-NH_2 \quad (III)$$

in which A has the above-mentioned meaning, is converted into a compound having the general formula IV

$$H2N-A-NH-Y \quad (IV)$$

in which Y represents a protecting group which is suitable for the amino group and can be easily cleaved off, for example the tert.-butyloxycarbonyl group and subsequently the compound of the general formula IV is reacted according to known methods with a compound of the general formula V

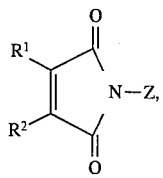

in which $R_1$ and $R_2$ have the meanings mentioned above and Z denotes a reactive group and subsequently the protecting group Y is again cleaved off.

The reaction of the diamines of the general formula III with suitable protecting group reagents, such as e.g. di-tert.-butyl-dicarbonate, tert.-butoxycarbonyl chloride or N-(tert.-butoxycarbonyl-oxy)phthalimide, is carried out in solvents such as e.g. dioxane, tetrahydrofuran, dimethylformamide or ethanol at temperatures of −20° C. to +100° C., preferably 0° C. to +25° C. according to known methods.

The reaction of compounds of formula IV with compounds of formula V is preferably carried out in basic solutions at temperatures of −20° C. to +80° C. Groups come into consideration as the reactive group Z which can be easily cleaved off by reaction with amines such as e.g. alkoxycarbonyl groups, for example the ethoxycarbonyl group.

The new compounds of formula I are employed as heterobifunctional reagents in particular for the production of conjugates. Hapten-peptide, hapten-protein, antigen-peptide, antigen-protein or antibody-effector conjugates come into consideration as conjugates. In the case of antibody-effector conjugates, an antibody is covalently bound for example to an effector molecule in which the effector can be an analyte, active substance, toxin or even an enzyme generating a signal.

The present invention also provides compounds of formula II in which Hap represents a binding partner which, as the analyte, is suitable for use in immunological methods of determination. Such binding partners are for example haptens or antigens which carry at least one carboxyl group or can be converted into a derivative carrying carboxyl groups such as e.g. the haptens cortisol, theophylline or digoxigenin. Antigens can be proteins or peptides. In principle, however, all those substances may be considered for the group Hap for which antibodies can be obtained which are directed against them. Particularly suitable are those which can be used for carrying out methods of determination according to the CEDIA technique described above. In particular, these substances can be analytes i.e. such compounds which occur in the serum of patients and whose determination is of diagnostic interest.

In general the term "haptens" is understood to include those molecules which are not directly suitable for binding antibodies but indirectly via binding to suitable immunological carriers. The following haptens are mentioned as examples: phenobarbital, diphenylhydantoin, carbamazepine, valproic acid, thyroxine (T4), triiodothyronine (T3), oestrone, oestradiol, progesterone, testosterone, aldosterone, folic acid, methyltetrahydrofolic acid or cyanocobalamin (vitamin B12).

The haptens or antigens defined above under Hap come into consideration for producing the amidoalkylmaleimide derivatives of the general formula II. For the reaction of the maleimides of the general formula I with suitable Hap derivatives it is expedient to first activate the carboxyl group present in Hap by conversion into a reactive derivative. This is carried out for example by reaction with N-hydroxysuccinimide ester in the presence of a condensing agent such as e.g. N,N-dicyclohexylcarbodiimide. The Hap-carboxylic acid-N-hydroxysuccinimide ester produced in this way is then reacted directly with the maleimido derivative of the general formula I to form the corresponding maleimide-hapten derivatives of the general formula II in a high yield. It is, however, also possible in principle to use other activating groups of the carboxyl group such as e.g. the imidazolyl, hydroxybenzotriazolyl, p-nitrophenyl or isobutoxycarbonyl groups.

In preferred embodiments of the compounds according to the present invention of the general formula II the immunological binding partner is a hapten such as e.g. a steroid hormone or a xanthine derivative, for example, cortisol, theophylline or digoxigenin. However, in principle, all those haptens can be used which carry a reactive carboxyl group. The carboxyl group can be present in a free form or in the form of activated derivatives such as, for example, anhydrides, esters or amides. It is, however, also possible to use those haptens as binding partners which originally did not contain a carboxyl group if the corresponding carboxyl group can be subsequently introduced into the hapten by chemical modification. Suitable modification reactions are known from the relevant state of the art.

In a further embodiment of the invention, compounds of the general formula II are provided in which the hapten is a steroid hormone. The detection of steroid hormones, such as e.g. oestrogen, testosterone, cortisones and cardiac glycosides which all have the steroid skeleton in common, plays an important role in diagnostics. The provision of antibodies against steroid hormones or against the corresponding hapten-peptide conjugates is therefore desirable for carrying out immunoassays.

It has been shown that the epitope of the hapten is not impaired by the derivatisation of the haptens to the compounds of the general formula II so that an antibody directed against the respective free hapten present in the sample to be determined also recognises the corresponding modified hapten-peptide conjugate to the same degree.

In addition, it has been shown that the derivatised hapten-peptide conjugates, which are obtained by reacting compounds of the general formula II with peptides or proteins containing sulfhydryl groups, associate with the enzyme acceptor EA to form the tetramer complexes of β-galactosidase without impairment of the binding properties. These in turn show no negative influence of the enzyme activity by the derivitisation of the enzyme, which is in principle present, and cleave possible substrates in the same way as unmodified β-galactosidase.

When employed for immunization the Hap derivatives of the general formula II are used. The hapten derivative is injected several times at intervals into an organism suitable for the formation of antibodies. In the course of this, antibodies are formed, a high percentage of which are directed against the hapten and do not show any cross-reactivity with the linking groups. The antibodies are then isolated from the organism and purified in ways which are generally known. The hapten derivatives according to the present invention of the general formula II are suitable for immunization in order to produce polyclonal antibodies as well as for the production of monoclonal antibodies.

Surprisingly, it was possible by using the hapten derivatives according to the present invention of the general formula II to obtain antibodies which show very little cross-reactivity with the bridging compound. The antibodies obtained have a high affinity to the hapten. When hapten derivatives according to the present invention are used for immunization, high antibody titres are obtained. Furthermore, the hapten-peptide conjugates according to the present invention are particularly well-suited for use in immunoassays. Since the antibodies show either no or only a very slight affinity to the bridging molecule and thus bind the hapten very specifically one obtains very exact results with these conjugates when used in immunoassays.

The hapten derivatives according to the present invention of the general formula II have the advantage that, on the one hand, they comprise the largely unchanged structure of the free hapten and, on the other hand, compared to derivatives which are e.g. known from the state of the art, they show a characteristic change in the bridging molecule. The use of the hapten derivatives according to the present invention thus enables heterologous linker techniques to be carried out in a simple and effective manner.

The present invention also concerns conjugates which can be produced by reacting the compounds of the general formula II with peptides and proteins. As peptides and proteins, those come into consideration which contain a sulfhydryl group or a cysteine group which react with the maleimido group of the compounds of formula II. Such derivatives are produced by generally known methods for the chemical modification of proteins. However, peptides are preferably used, in particular the enzyme donors ED which can be used in the CEDIA technique described above. The modification of peptides or proteins is effected by well-known methods in suitable buffers, e.g. phosphate buffer at temperatures between 0° C. and 40° C., preferably at 15°–25° C., by incubation with compounds of formula II for a period of 1–24 h. The production of different ED-derivatives is disclosed in U.S. Pat. No. 4,708,929 or Clin. Chem. 32 (9), 1986, 1637–1641 or they are obtainable from Microgenics Corp., Concord, Calif. (USA).

The invention therefore also concerns the use of a hapten-peptide conjugate according to the present invention when carrying out immunoassays.

The following examples elucidate the invention on the basis of concrete examples for carrying it out.

EXAMPLE 1 a) N-(tert.-butyloxycarbonyl)ethane-1,2-diamine 12 g (0.2 mol) ethylenediamine is dissolved in 200 ml dioxane/water (50/50 v/v). A solution of 21.8 g (0.1 mol) di-tert.-butyl-dicarbonate in 100 ml dioxane is added dropwise within 1.5 h while stirring and cooling in an ice bath. It is stirred for a further hour at room temperature, then diluted with 500 ml water and extracted with 1 l acetic ester. The organic solution is washed three times with 200 ml water and extracted twice with 300 ml 0.1n HCl. The combined HCl phases are adjusted to pH 10.0 with 2n NaOH and extracted with 600 ml acetic ester. The organic solution is washed again with 300 ml water, dried with 20 g $Na_2SO_4$ and evaporated in a water-jet vacuum.

Yield: 1.35 g viscous oil (corresponds to 8.4% of the theoretical yield with respect to di-tert.-butyl-dicarbonate).

TLC: silica gel, methanol/acetic ester (66/33 v/v), spray with ninhydrin spray (Merck Company, Darmstadt); $R_f$=0.14.

b) N-(tert.-butyloxycarbonyl)pentane-1,5-diamine acetate 20.4 g (0.2 mol) pentane-1,5-diamine is dissolved in 200 ml dioxane/water (50/50 v/v). A solution of 21.8 g (0.1 mol) di-tert.-butyl-dicarbonate in 100 ml dioxane is added dropwise within 1.5 h while stirring and cooling in an ice bath. It is stirred for a further 2 hours at 0° C. and subsequently for a further 18 hours at 20° C., then diluted with 500 ml water and extracted with 1 l acetic ester. The organic solution is washed twice with 200 ml water, dried with 50 g $Na_2SO_4$ and evaporated in a rotary evaporator. The semisolid residue is digested with 200 ml 10% acetic acid and the undissolved bis-BOC-pentane-1,5-diamine is filtered off by suction. The filtrate is evaporated and the remaining viscous product is dried for 4–6 h in a high vacuum.

Yield: 11.6 g (corresponds to 44% of the theoretical yield with respect to di-tert.-butyl-dicarbonate)

TLC: silica gel, methanol/chloroform/ammonia 45/45/10 v/v/v), spray with ninhydrin spray (Merck Company, Darmstadt); $R_f$=0.65.

EXAMPLE 2 a) N-(tert.-butyloxycarbonyl)-2-(N-maleinimido)ethylamine 0.8 g (5 mmol) of the compound produced according to Example 1a is dissolved in 25 ml saturated sodium bicarbonate solution. The solution is filtered over a folded filter and cooled to 0° C. Subsequently 0.84 g (5 mmol) N-(ethoxycarbonyl)maleinimide (produced according to the method of O. Keller and J. Rudinger, Helv. Chim. Acta 58 (1975), 531–541) is added while stirring and it is left to stir for a further 15 min at room temperature. During this the N-(ethoxycarbonyl)maleinimide dissolves completely after a short time while the title compound precipitates during the course of the reaction. 40 ml THF is added and stirred for a further 45 min at room temperature. Afterwards it is adjusted to pH 6.0 with 1n HCl, extracted twice with 50 ml acetic ester and the extract is dried with 5 g $Na_2SO_4$. After evaporation in a water-jet vacuum the title compound is obtained as a colourless, solid residue.

Yield: 1.1 g (92% of the theoretical yield).

TLC: silica gel, chloroform/acetic ester (66/33 v/v), spray with 0.1% $KMnO_4$ solution; $R_f$=0.50.

b) N-(tert.butyloxycarbonyl)-5-(N-maleinimido)pentylamine 13.1 g (50 mmol) of the compound prepared according to Example 1b is dissolved in 250 ml saturated sodium carbonate solution. The solution is filtered over a folded filter and cooled to 0° C. 8.4 g (50 mmol) N-(ethoxycarbonyl)-maleinimide is added while stirring and is left to stir for a further 15 min at room temperature, during which the N-(ethoxycarbonyl)-maleinimide dissolves completely after a short time. Subsequently 400 ml tetrahydrofuran is added together with 250 ml saturated sodium carbonate solution and it is allowed to react for a further 1 h. The solution is then extracted with 2×500 ml acetic ester, the extract is washed with 500 ml water and dried with 50 g $Na_2SO_4$. After evaporation in a rotary evaporator the product is obtained as a viscous oil which is dried in a high vacuum.

Yield: 9.6 g (corresponds to 68% of the theoretical yield).

TLC: silica gel, n-butanol/glacial acetic acid/water 40/10/50 (v/v/v), spray with 0.1% $KMnO_4$ solution; $R_f$=0.85.

EXAMPLE 3 a) 2-(N-maleinimido)ethylamine hydrochloride 0.96 g (4 mmol) of the BOC-amino compound from Example 2a is dissolved in 25 ml 2m HCl in dioxane and left to stand at room temperature. The product 4 starts to precipitate out within 30–60 minutes. It is allowed to stand for 24 h at room temperature, the crystallizate is siphoned off, washed with ca 10 ml acetic ester and dried in a desiccator over CaCl$_2$ and paraffin.

Yield: 0.58 g colourless, finely crystalline powder (82% of the theoretical yield).

TLC: silica gel, n-butanol/glacial acetic acid/water (40/10/50 v/v/v), spray with ninhydrin spray (Merck Company, Darmstadt); $R_f$=0.22.

C$_6$H$_9$ClN$_2$O$_2$ (176.60); calculated: C 40.81; H 5.14; N 15.86. found: C 40.60; H 5.29; N 15.46.

b) 5-(N-maleinimido)pentylamine hydrochloride 8.46 g (30 mmol) of the BOC amino compound prepared according to Example 2b is dissolved in 100 ml 2m HCl in dioxane and left to stand at room temperature. The product starts to precipitate out within 30–60 min. It is allowed to stand for 24 h at room temperature, the crystallizate is siphoned off, washed with ca 50 ml acetic ester and dried in a desiccator over CaCl$_2$ and paraffin.

Yield: 4.7 g colourless, finely crystalline powder (corresponds to 72% of the theoretical yield).

TLC: silica gel, n-butanol/glacial acetic acid/water (40/10/50 v/v/v), spray with ninhydrin spray (Merck Company, Darmstadt); $R_f$=0.22

C$_9$H$_{15}$ClN$_2$O$_2$ (218.69); calculated: C 49.43; H 9.91; N 12.81. found: C 49.19; H 9.99; N 12.59.

EXAMPLE 4

Production of hapten-carboxlic acid derivatives

The following hapten carboxylic acids were produced according to instructions from the literature:

a) Cortisol-3-(O-carboxymethyl)-oxime from cortisol and carboxymethylhydroxylamine-hemihydrochloride in ethanol Lit.: A. Tsuji et al., Steroids 24 (1974), 739–51

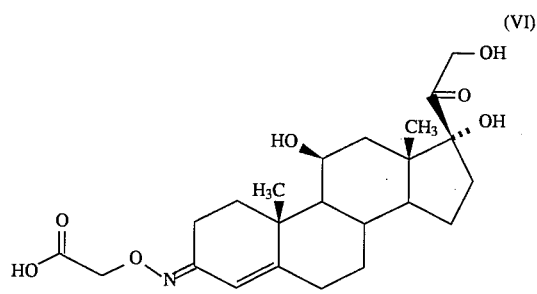

b) 3-O-succinyl-digoxigenin from digoxigenin and succinic acid-anhydride Lit.: G. C. Oliver et al., J. Clin. Invest. 47 (1968), 1035–1042.

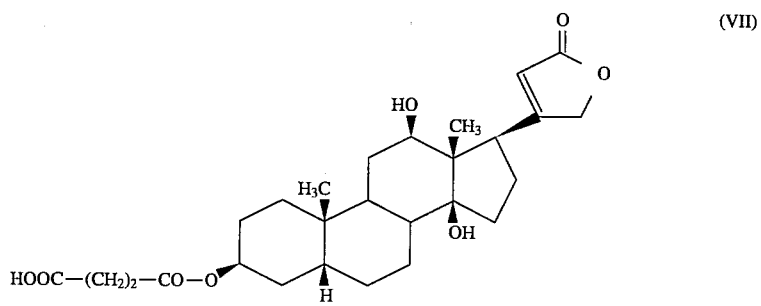

c) Digoxin-4'''-glutaryl-hydroxysuccinimide ester from digoxin and glutaryl-w-orthotrimethyl ester-w'-hydroxysuccinimide ester in THF. Lit.: H. G. Batz et al., DE-A-2,537,129 or U.S. Pat. No. 4,133,949, U.S. Pat. No. 4,436,828

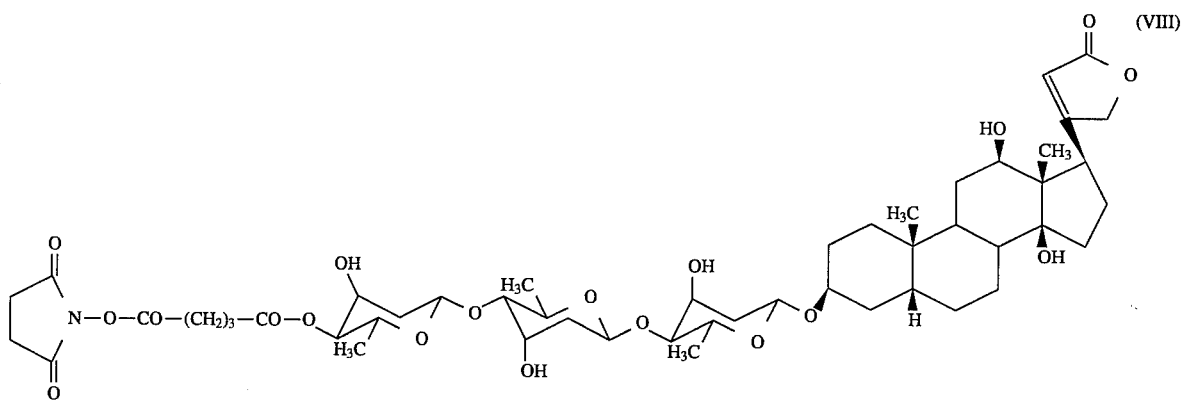

d) 8-(3-carboxypropyl)-theophylline from 4,5-diamino-1,3-dimethylpyrimidine-2,6-dione and glutaric acid-anhydride. C. E. Cook et al., Res. Commun. Chem. Pathol. Pharmacol. 13 (1976), 497–505

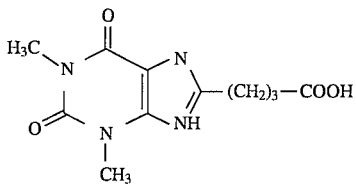

(IX)

e) 5-ethyl-5-phenyl-1-(3-carboxypropyl)barbituric acid (1-(3-carboxypropyl)-phenobarbital) from sodium phenobarbital and 4-bromobutyric acid-ethyl ester C. E. Cook et al., Quantitative Analogical Studies in Epilepsy, P. Kellaway and Ingemar Petersen (ed.), Raven Press, New York 1976, p.39–58.

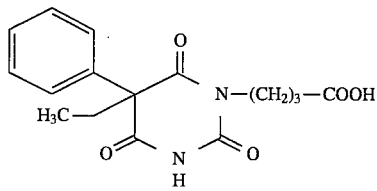

(X)

EXAMPLE 5

Hapten-carboxylic acid-N-hydroxysuccinimide ester

General Instructions For Production 0.5 mmol hapten-carboxylic acids produced according to the Examples 4 a,b,d,e is dissolved together with 63 mg (0.55 mmol) N-hydroxysuccinimide in 10 ml absolute DMF and 1.13 mg (0.55 mmol) N,N-dicyclohexyl-carbodiimide is added. It is stirred for 4 h at room temperature, filtered and the solution is evaporated in a vacuum. The residue is taken up in 20 ml THF and any remaining undissolved N,N-dicyclohexyl-urea residues are removed by filtration. The solutions of the hapten-carboxylic acid-N-hydroxysuccinimide ester are employed in this form for the next step.

EXAMPLE 6

Hapten-carboxylic acid-[2-(N-maleinimido)ethylamide]

General Instructions 88 mg (0.5 mmol) 2-(N-maleinimido)ethylamine is added to the solution of the activated haptens from Example 5. While stirring 51 mg (0.5 mmol) triethylamine is added dropwise; afterwards it is allowed to stir for a further 6 h at room temperature. The solution is evaporated in a vacuum and the hapten-maleinimide compound II A-C is purified by column chromatography on a silica gel column (2.5×30 cm) with a suitable solvent. The corresponding fractions are collected and evaporated in a vacuum.

The solution of the compound produced according to Example 5d is evaporated to half volume in a vacuum and the precipitate is filtered off. The solvent is then completely removed in a vacuum. The residue is digested with isopropanol, the solid product is siphoned off and dried in a desiccator.

The following products are obtained:

a) 2-(N-maleinimido)ethylamide from cortisol (3-O-carboxymethyl)-oxime

Eluant: acetic ester/methanol (90/10 v/v). Yield: 180 mg (64% of the theoretical yield). TLC: silica gel, acetic ester/methanol (90/10 v/v); $R_f$=0.60

$C_{29}H_{39}N_3O_8$ (557.63); calculated: C 62.46; H 7.05; N 7.54. found: C 62.20; H 7.10; N 7.31.

b) 2-(N-maleinimido)ethylamide from 3-O-malonyl-digoxigenin

Eluant: acetic ester/petrol ether/ethanol (40/40/20 v/v/v). Yield: 145 mg (47% of the theoretical yield). TLC: silica gel, acetic ester/petrol ether/ethanol (40/40/20 v/v/v); $R_f$=0.58.

$C_{33}H_{44}N_2O_9$ (612.71); calculated: C 64.69; H 7.24; N 4.57. found: C 64.60; H 7.44; N 4.29.

c) 2-(N-maleinimido)ethylamide from digoxin-4'''-glutaryl-hydroxysuccinimide ester Eluant: acetic ester/petrol ether/methanol (40/40/20 v/v/v).

Yield: 220 mg (43% of the theoretical yield).

TLC: silica gel, acetic ester/petrol ether/methanol (40/40/20 v/v/v); $R_f$=0.48.

$C_{52}H_{76}N_2O_{18}$ (1017.15); calculated: C 61.40; H 7.53; N 2.75. found: C 61.31; H 7,68; N 2.50.

d) 2-(N-maleinimido)ethylamide from 8-(3-carboxypropyl)-theophylline

Yield: 120 mg (62% of the theoretical yield).

TLC: silica gel, butanol/glacial acetic acid/water (40/10/50 v/v/v); $R_f$=0.79

$C_{17}H_{20}N_6O_5$ (388.38); calculated: C 52.57; H 5.19; N 21.64. found: C 52.41; H 5.01; N 21.74.

e) 2-(N-maleinimido)ethylamide from 1-(3-carboxypropyl)-phenobarbital

Yield: 95 mg (44% of the theoretical yield).

TLC: silica gel, acetic ester/methanol (90/10 v/v); $R_f$=0.83

$C_{22}H_{24}N_4O_6$ (440.46); calculated: C 59.99; H 5.49; N 12.72. found: C 59.60; H 5.79; N 12.55.

EXAMPLE 7

Production of Hapten-Peptide Conjugates

200 μg enzyme donor ED4, described in U.S. Pat. No. 4,708,929 (24.11.1987), is dissolved in 150 ml 0.05m sodium phosphate buffer, pH 6.5 and 20 mg activated hapten II A-D in 20 ml acetonitrile is added. The solution is stirred for 4 h at room temperature. The conjugate is purified by HPLC on a C-18 column (Dynamax 60A 8, 4.6×250 mm; gradient: 20–100% B, B=acetonitrile/water 65/35 v/v). The retention time of the non-conjugated ED4 is 25.35 min in this system. The corresponding fractions are collected and dialyzed against 5 l water. The solution of the conjugate can be used in this form for the immunological test methods mentioned in U.S. Pat. No. 4,708,929 or for alternative methods.

The following were obtained in this way:

a) Theophylline-8-acetic acid- [2-(N-maleinimido)ethylamide]-ED4 conjugate Yield: 12 μg; retention time (HPLC): 26.91 min.

b) Phenobarbital-1-butyric acid- [2-(maleinimido)ethylamide]-ED4 conjugate Yield: 155 μg; retention time (HPLC): 23.78 min.

EXAMPLE 8

Synthesis of cortisol-3-carboxylic acid-[2-(N-maleinimido)ethylamide]-β-Gal immunogen 500 mg β-Gal (Boehringer Mannheim No. 570 079) is dissolved in 50 ml 0.1n potassium phosphate buffer pH 6.0 at 20° C. and 110 mg of the cortisol compound in 10 ml dioxane produced according to Example 4a is added dropwise while stirring vigorously. After the addition is completed it is allowed to stir for a further ca 16 h, then the solution is applied to an AcA 202 Ultrogel-column (800 ml volume) and eluted with 0.01 n potassium phosphate buffer pH 7.0, 0.9% NaCl. The fractions containing protein are collected and the concentration is determined by UV absorption at 280 nm (protein concentration=A×1.9 mg/ml). The yield of the immunogen is typically 350 to 450 mg. The protein conjugate is lyophilized and stored at −20° C.

We claim:

1. An amidoalkylmaleimide compound of formula II

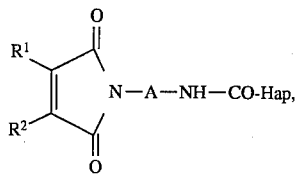

in which Hap is a residue formed by amidation of a hapten or antigen carrying one or several carboxyl groups or carboxyl derivatives, $R_1$ and $R_2$ are the same or different and denote a $C_{1-C4}$ alkyl group or a hydrogen atom and A is a straight-chain or branched, saturated or unsaturated alkylene group having 2–6 C atoms which is uninterrupted or is interrupted by an oxygen or a sulphur atom or a carbonyl group.

2. Amidoalkyl-maleimides of claim 1, wherein the hapten is a steroid.

3. A peptide or protein conjugate compound as produced by reaction of an amidoalkylmaleimide of formula II

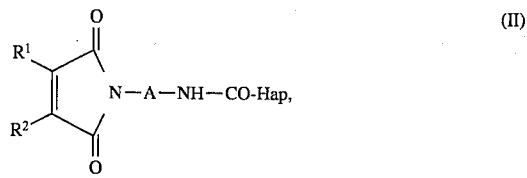

with a peptide or protein carrying at least one sulfhydryl group wherein in Formula II Hap is a hapten, $R_1$ and $R_2$ are the same or different and are $C_1$–$C_4$-alkyl or hydrogen and A is a straight-chain or branched, saturated or unsaturated $C_2$–$C_6$-alkylene, which alkylene is uninterrupted or is interrupted by an oxygen or a sulphur atom or a carbonyl.

4. The conjugate compound of claim 3 wherein the peptide is an enzyme-donor polypeptide of β-galactoside.

5. The conjugate compound of claim 4 wherein the enzyme-donor polypeptide is ED4.

6. The conjugate compound of claim 3 wherein the peptide is β-galactoside.

7. The conjugate compound of claim 3 wherein $R_1$ and $R_2$ in formula II are the same and are hydrogen.

8. The conjugate compound of claim 3, wherein A in formula II is —$(CH_2)_2$—, —$(CH_2)_m$—$(CH_3)$—$(CH_2)_o$—, $(CH_2)_m$—$C(CH_3)_2$—$(CH_2)_o$—, $(CH_2)_m$—X—$(CH_2)_o$— or —$(CH_2)_m$—CH=CH—, wherein X is O, S or CO, n is 2–6, m=o=1–4 and m +o=2–5.

9. The conjugate compound of claim 3 wherein A is —$(CH_2)_n$— wherein n is 2, 3, 4 or 5, or A is —$CH_2$—O—$CH_2$—, $CH_2$—S—$CH_2$— or —$CH_2$—CO—$CH_2$.

10. The conjugate compound of claim 3 designated theophylline-8-acetic acid-[2-(N-maleinimido)ethylamide]-ED4, phenobarbital-1-butyric acid-[2-(N-maleinimido)ethylamide]-ED4 or cortisol-3-carboxylic acid-[2-(N-maleinimido)ethylamide]-β-Gal.

* * * * *